United States Patent [19]

Jochum et al.

[11] Patent Number: 4,532,268

[45] Date of Patent: Jul. 30, 1985

[54] IMIDAZOLE AGENT FOR RETARDING THE POLYMERIZATION OF AZIRIDINE COMPOUNDS

[75] Inventors: Peter Jochum, Seefeld; Heijo Hubner, Worthsee; Oswald Gasser, Seefeld, all of Fed. Rep. of Germany

[73] Assignee: ESPE, Fabrik pharmazeutischer Praparate GmbH, Seefeld, Fed. Rep. of Germany

[21] Appl. No.: 556,772

[22] Filed: Dec. 1, 1983

[30] Foreign Application Priority Data

Dec. 6, 1982 [DE] Fed. Rep. of Germany ....... 3245052

[51] Int. Cl.³ .................... C08L 79/00; C08L 79/02
[52] U.S. Cl. .................... 523/109; 523/120; 528/422; 528/424
[58] Field of Search ............... 523/109, 120; 528/424, 528/422

[56] References Cited

U.S. PATENT DOCUMENTS 3,751,395 8/1973 Schmitt et al. ..................... 523/109

Primary Examiner—Harold D. Anderson
Attorney, Agent, or Firm—Birch, Stewart, Kolasch & Birch

[57] ABSTRACT

Imidazoles in dissolved form act as an agent for retarding the gelation of the polymerization of aziridine compounds initiated with sulfonium salts. The composition is particularly useful in dentistry applications, such as in the preparation of impressions and provisional denture parts.

19 Claims, No Drawings

IMIDAZOLE AGENT FOR RETARDING THE POLYMERIZATION OF AZIRIDINE COMPOUNDS

In order to produce precise impressions, especially in dentistry, working models particularly for dental technology, and of temparary dental crowns and bridges, aziridine-containing substances are polymerized as described, for example in U.S. Pat. Nos. 3,453,242 and 4,093,555. As described in these patents, the aziridine-containing compounds are used together with suitable fillers, dyestuffs, and further adjuvants.

For several applications, especially in dentistry and dental technology, it is significant that the processing period of the initiated mixture and the termination of the polymerization reaction can be determined within relatively narrow limits. This is the case, for example, in the preparation of a jaw impression. The processing period of the initiated mixture must be sufficiently long that the material may be placed on an impression tray and can then be brought into the patient's mouth. Thereafter, the polymerization should be terminated as soon as possible in order that the impression can be removed after a short time without undergoing any dimensional change with the required time being tolerable for the dentist and the patient. The situation is similar in the case of an intraoral preparation of temporary dental crowns and bridges, and also in the preparation of a jaw model by the dental technician.

As disclosed in U.S. Pat. No. 4,167,618, it has been known to use as polymerization initiators for these aziridine compounds sulfonium salts containing in the β-position to the central sulfur atom an electron-attracting group and a non-nucleophilic anion.

The processing period (potlife) and setting period (curing time) of the mixtures can be influenced within relatively wide limits with the use of sulfonium salts as polymerization initiators owing to the chemical constitution of the sulfonium molecule.

When a less active sulfonium initiator is employed, the available processing time will be sufficiently long, but setting will take place so slowly that when used for taking the impression, especially in the dental medicine area, an intolerable delay of curing of the rubber-elastic impression composition will occur. An active sulfonium salt effects rapid termination of the rubber formation so that an impression, for example, can be taken out of the mouth after a short time without any deformation of the impression occurring. However, then the processing period is so short that there is the risk, particularly at warm temperatures such as in the summer, that the impression will be introduced into the mouth when already in the reaction phase and thus when the composition already exhibits a certain resilience, or displacements in the gum region are to be expected.

In the selection of the sulfonium salt, additional requirements have to be taken into account besides the desired temporal course of the polymerization including the availability of the starting components to attain the desired substitution, possibilities of a suitable control of the reaction, thermal and hydrolytic stability of the product, and the solubility of the sulfonium salt in the selected aziridine compound. Frequently, it is not possible to find a sulfonium salt that effects the desired course of the polymerization without major deviations. It is a further disadvantage that the course of the polymerization can be influenced only to a small extent by variations in the quantity of the sulfonium salt initiator.

It has been known that amines can retard the polymerization of aziridine compounds. However, the common organic amines (e.g., tributylamine, benzylamine and triethanolamine) either do not show any effect whatsoever, or retard curing so much that they cannot be employed.

Therefore, the problem underlying the invention is the provision of compounds that retard gelling of the polymerization of aziridine compounds initiated with sulfonium salts without substantially extending the curing period.

In this regard, and in accordance with the present invention, it has been found that imidazoles prolong the processing period of aziridine compounds mixed with sulfonium initiators without substantially infuencing the curing thereof.

Therefore, the invention is directed to a composition comprising at least one aziridine compound which is polymerizable with sulfonium salts, said composition containing at least one imidazole compound in dissolved form. The invention further relates to the use of imidazoles capable of dissolving in aziridine compounds as agents for retarding gelation of the polymerization of aziridine compounds initiated with sulfonium salts.

Depending on the concentration of the imidazole derivative, the attainable retardation of curing ranges from about 15 seconds to several minutes. The addition of imidazoles to the aziridine-containing polymerizable compositions according to the invention permits the use of a highly reactive sulfonium initiator (preferably having a nitrile substituent located in the β-position with respect to the central sulfur atom), thus simultaneously providing sufficient processing time and rapid curing of the composition.

In principle, imidazole itself and all 1-substituted imidazole derivatives are suited for the purpose of the invention, provided they are soluble in the particular aziridine compound(s) employed. Imidazoles more sparingly soluble in the aziridine compounds employed may be dissolved by the addition of plasticizers such as phthalic acid esters, as solubilizers. Preferably, 1-substituted imidazoles are employed.

For example, the imidazoles used according to the invention may have the general formula

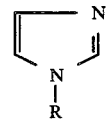

wherein R represents:
(a) $C_1$–$C_{18}$ alkyl
(b) substituted $C_1$–$C_{18}$ alkyl
(c) $C_3$–$C_{12}$ cycloalkyl
(d) substituted $C_3$–$C_{12}$ cycloalkyl
(e) $C_2$–$C_{18}$ alkenyl
(f) substituted $C_2$–$C_{18}$ alkenyl
(g) substituted phenyl
(h) H The alkyl group in (a) and (b) preferably has from 1 to 12 carbon atoms, the cycloalkyl group in (c) and (d) has from 3 to 6, especially 5 or 6, carbon atoms, and the alkenyl group in (e) and (f) has from 2 to 12 carbon atoms, vinyl and allyl being preferred alkenyl groups.

Substituents for the groups (b), (d), (f) and (g) include ester groups, e.g., $C_1$–$C_{18}$ alkoxycarbonyl groups; amidocarbonyl groups, e.g., $C_1$–$C_{18}$ alkylamidocarbonyl groups or aralkylamidocarbonyl groups such as benzylamidocarbonyl; acylamido groups, e.g., $C_2$–$C_{18}$ alkanoylamido or benzoylamido groups; acyloxy groups, e.g., $C_2$–$C_{18}$ alkanoyloxy or benzoyloxy groups; and ether groups, preferably with 1 to 18 carbon atoms, e.g., $C_1$–$C_{18}$ alkoxy groups. Also, optionally substituted phenyl moieties and 1-imidazolyl groups are suitable as substituents for the (b), (d), (f) and (g) groups.

Examples of suitable imidazole compounds are 1-methylimidazole, 1-(n-butyl)imidazole, 1-decylimidazole, 1-laurylimidazole, 1,ω-bis(1-imidazolyl)-$C_1$–$C_{10}$ alkanes such as 1,2-bis(1-imidazolyl)ethane and 1,10-bis(1-imidazolyl)decane, 11-(1-imidazolyl)undecanoic acid benzylamide, 1-cyclohexylimidazole, 1-benzylimidazole, 1-(2-ethoxyethyl)imidazole, 1-(4-methoxyphenyl)imidazole, and 1-[3-(2-ethylhexanoyl)amidopropyl]-imidazole.

The imidazoles are employed in an amount of from about 0.01 to 3%, preferably 0.05 to 2% by weight, based on the weight of the aziridine compounds.

The imidazoles used according to the invention are prepared by means of known processes described, for example, in J. Chem. Soc., 1963, 2197 and Helv. Chim. Acta, 42, 1845 (1959).

The compounds disclosed in U.S. Pat. Nos. 3,453,242 and 4,093,555 can be employed as the aziridine compounds, e.g., polyethers with terminal aziridino groups and bisphenol-A derivatives with terminal aziridino groups. As sulfonium initiators, those disclosed in U.S. Pat. No. 4,167,618 are suitable, the sulfonium salts containing nitrile or ester groups in the β-position with respect to the sulfur atom being preferred. The amounts thereof range from about 1 to 8% by weight for aziridine compounds as described in U.S. Pat. No. 4,093,444; for other aziridine compounds the amount employed ranges from about 2 to 20% by weight, based on the weight of the aziridine compounds.

The aziridine compounds mixed with the imidazoles used according to the invention are used for producing precise impressions and working models, and also primarily in dental impression compositions on the basis of polyethers having terminal aziridino groups. The preparation of such aziridino polyethers is described in U.S. Pat. No. 3,453,242. Fillers, plasticizers, dyestuffs, taste-improving additives and other customary dental adjuvants are added to said aziridino polyethers in the preparation of compositions used for impressions.

Structurally related compounds, such as N-substituted pyrazoles and triazoles, do not exhibit the effect desirable for the purposes of the invention (that is, retardation of the beginning of gelling upon the addition of the sulfonium salt to the aziridine compound).

The following Examples are given merely as illustrative of the invention and are not to be considered as limiting. The periods of time stated in the Examples were measured from the beginning of mixing of the aziridino component with the sulfonium initiator.

EXAMPLE 1

1.0 Gram of a polyether having terminal aziridino groups and having an average molecular weight of about 6500 and the preparation of which is described in U.S. Pat. No. 3,453,242 (Example 13) is mixed with 4 mg of 1-methylimidazole. This mixture is then homogeneously blended with 0.08 g of β-(S-lauryl-S-ethylsulfonium)butyronitrile fluoroborate. After 3 minutes gelling occurs, and after 5.5 minutes a nontacky, rubber-elastic composition has formed.

COMPARATIVE EXAMPLE 1

The process of Example 1 is repeated without the addition of the imidazole. At a room temperature of about 23° C. gelling occurs after 1 minute and 50 seconds; after 4 minutes and 30 seconds, a nontacky, rubber-elastic composition has formed.

EXAMPLE 2

1.0 Gram of the aziridino polyether used in Example 1 is mixed with 8 mg of 1-laurylimidazole. Thereafter, 0.16 g of a 1:1 mixture of diethylhexyl phthalate and the sulfonium salt mentioned in Example 1 are homogeneously incorporated therein. After 3 minutes the composition starts gelling, and after 5 minutes and 30 seconds it has hardened to a nontacky, rubber-elastic composition.

EXAMPLE 3

For the production of an impression composition for dental purposes, 800 g of the bifunctional aziridine compound mentioned in Example 1 are masticated with 150 g of fine kieselguhr; moreover, 3.2 g of 1-methyl imidazole are added thereto.

30 g of the paste are mixed with 4.8 g of a 1:1 mixture of diethylhexyl phthalate and the sulfonium salt described in Example 1. The dentist has 3 minutes in order to bring the impression material into the patient's mouth by means of a suitable tray. After 5 minutes and 30 seconds, the rubber formation is completed to such an extent that the impression can be taken out of the patient's mouth without any risk of undergoing deformation.

EXAMPLE 4

In 1.0 g of the aziridino polyether mentioned in Example 1, 0.5 mg of 1-methyl imidazole are dissolved. Thereafter, 0.2 g of a 1:1 mixture of acetyl tributyl citrate and 2-ethylhexyl oxycarbonylmethyl ethylsulfonium propionic acid tetradecyl ester fluoroborate are homogeneously incorporated therein. Gelling occurs after 3 minutes; after 9 minutes a nontacky, rubber-elastic composition has formed.

COMPARATIVE EXAMPLE 2

The process of Example 4 is repeated without the addition of the imidazole. Gelling occurs after 2 minutes and 40 seconds; after 8 minutes a nontacky, rubber-elastic composition has formed.

The invention being thus described, it will be obvious that the same may be varied in many ways. Such variations are not to be regarded as a departure from the spirit and scope of the invention, and all such modifications as would be obvious to one skilled in the art are intended to be included within the scope of the following claims.

We claim:

1. A dental composition comprising at least one aziridine compound polymerizable with a sulfonium salt initiator and at least one imidazole compound dissolved directly in said aziridine compound or by action of a plasticizer.

2. A dental composition according to claim 1, wherein the imidazole compound has the formula:

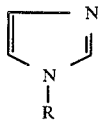

wherein R is unsubstituted or substituted $C_1-C_{18}$ alkyl, unsubstituted or substituted $C_3-C_{12}$ cycloalkyl, unsubstituted or substituted $C_2-C_{18}$ alkenyl, substituted phenyl or hydrogen.

3. A dental composition according to claim 1, wherein the amount of the imidazole compound present in the composition is from about 0.01 to 3% by weight based on the weight of the at least one aziridine compound.

4. A dental composition comprising at least one polymerizable aziridine compound, a sulfonium salt polymerization initiator and at least one imidazole compound dissolved in said aziridine compound.

5. A dental composition according to claim 4, wherein the sulfonium salt initiator has a nitrile group in the $\beta$-position with respect to the central sulfur atom therein.

6. A dental composition according to claim 4, wherein the imidazole compound has the formula:

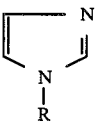

wherein R is unsubstituted or substituted $C_1-C_{18}$ alkyl, unsubstituted or substituted $C_3-C_{12}$ cycloalkyl, unsubstituted or substituted $C_2-C_{18}$ alkenyl, substituted phenyl or hydrogen.

7. A dental composition according to claim 4, wherein the amount of the imidazole compound present in the composition is from about 0.01 to 3% by weight based on the weight of the at least one aziridine compound.

8. A dental composition according to claim 4, wherein the aziridine compound is a polyether having terminal aziridino groups or a bisphenol A derivative having terminal aziridino groups.

9. A dental composition according to claim 2, wherein said $C_1-C_{18}$ alkyl, said $C_3-C_{12}$ cycloalkyl, said $C_2-C_{18}$ alkenyl or said phenyl is substituted with a member selected from the group consisting of $C_1-C_{18}$ alkoxycarbonyl, $C_1-C_{18}$ alkylamidocarbonyl, benzylamidocarbonyl, $C_2-C_{18}$ alkanoylamido, benzoylamido, $C_2-C_{18}$ alkanoyloxy, benzoyloxy and $C_1-C_{18}$ alkoxy.

10. A dental composition according to claim 1, wherein said at least one imidazole compound is a member selected from the group consisting of 1-methylimidazole, 1-(n-butyl)imidazole, 1-decylimidazole, 1-laurylimidazole, 1,ω-bis(1-imidazolyl)-$C_1-C_{10}$ alkanes, 1,2-bis(1-imidazolyl)ethane, 1,10-bis(1-imidazolyl)decane, 11-(1-imidazolyl)undecanoic acid benzylamide, 1-cyclohexylimidazole, 1-benzylimidazole, 1-(2-ethoxyethyl)imidazole, 1-(4-methoxyphenyl)imidazole, and 1-[3-(2-ethylhexanoyl)amidopropyl]-imidazole.

11. A dental composition according to claim 6, wherein said $C_1-C_{18}$ alkyl, said $C_3-C_{12}$ cycloalkyl, said $C_2-C_{18}$ alkenyl or said phenyl is substituted with a member selected from the group consisting of $C_1-C_{18}$ alkoxycarbonyl, $C_1-C_{18}$ alkylamidocarbonyl, benzylamidocarbonyl, $C_2-C_{18}$ alkanoylamido, benzoylamido, $C_2-C_{18}$ alkanoyloxy, benzoyloxy and $C_1-C_{18}$ alkoxy.

12. A dental composition according to claim 4, wherein said at least one imidazole compound is a member selected from the group consisting of 1-methylimidazole, 1-(n-butyl)-imidazole, 1-decylimidazole, 1-laurylimidazole, 1,ω-bis(1-imidazolyl)-$C_1-C_{10}$ alkanes, 1,2-bis(1-imidazolyl)ethane, 1,10-bis(1-imidazolyl)decane, 11-(1-imidazolyl)undecanoic acid benzylamide, 1-cyclohexylimidazole, 1-benzylimidazole, 1-(2-ethoxyethyl)imidazole, 1-(4-methoxyphenyl)imidazole, and 1-[3-(2-ethylhexanoyl)amidopropyl]-imidazole.

13. A method for retarding the gelation of the polymerization of at least one aziridine compound initiated with a sulfonium salt which comprises adding thereto at least one imidazole compound capable of being dissolved in said at least one aziridine compound.

14. The method of claim 13, wherein the imidazole compound has the formula:

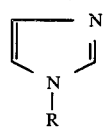

wherein R is unsubstituted or substituted $C_1-C_{18}$ alkyl, unsubstituted or substituted $C_3-C_{12}$ cycloalkyl, unsubstituted or substituted $C_2-C_{18}$ alkenyl, substituted phenyl or hydrogen.

15. The method of claim 13, wherein from about 0.01 to 3% weight of the imidazole compound based on the weight of the at least one aziridine compound is added to the composition containing the aziridine compound.

16. A method according to claim 14, wherein said $C_1-C_{18}$ alkyl, said $C_3-C_{12}$ cycloalkyl, said $C_2-C_{18}$ alkenyl or said phenyl is substituted with a member selected from the group consisting of $C_1-C_{18}$ alkoxycarbonyl, $C_1-C_{18}$ alkylamidocarbonyl, benzylamidocarbonyl, $C_2-C_{18}$ alkanoylamido, benzoylamido, $C_2-C_{18}$ alkanoyloxy, benzoyloxy and $C_1-C_{18}$ alkoxy.

17. A method according to claim 13, wherein said at least one imidazole compound is a member selected from the group consisting of 1-methylimidazole, 1-(n-butyl)imidazole, 1-decylimidazole, 1-laurylimidazole, 1,ω-bis(1-imidazolyl)-$C_1-C_{10}$ alkanes, 1,2-bis(1-imidazolyl)ethane, 1,10-bis(1-imidazolyl)decane, 11-(1-imidazolyl)undecanoic acid benzylamide, 1-cyclohexylimidazole, 1-benzylimidazole, 1-(2-ethoxyethyl)imidazole, 1-(4-methoxyphenyl)imidazole, and 1-[3-(2-ethylhexanoyl)amidopropyl]-imidazole.

18. A process for preparing dental impressions, models, crowns or bridges, wherein a dental composition is cured which contains at least one aziridine compound polymerizable with a sulfonium salt initiator, a sulfonium salt initiator and at least one imidazole compound which is dissolved directly in said aziridine compound or by action of a plasticizer.

19. A process as in claim 18, wherein the imidazole compound has the formula:

7

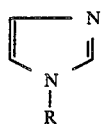

wherein R is unsubstituted or substituted $C_1$-$C_{18}$ alkyl, unsubstituted or substituted $C_3$-$C_{12}$ cycloalkyl, unsubstituted or substituted $C_2$-$C_{18}$ alkenyl, substituted phenyl or hydrogen.

* * * * *

8

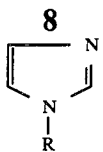

wherein R is unsubstituted or substituted $C_1$-$C_{18}$ alkyl, unsubstituted or substituted $C_3$-$C_{12}$ cycloalkyl, unsubstituted or substituted $C_2$-$C_{18}$ alkenyl, substituted phenyl or hydrogen.

* * * * *